United States Patent [19]
Johnson et al.

[11] Patent Number: 6,091,978
[45] Date of Patent: Jul. 18, 2000

[54] REMOVABLE CAP FOR TISSUE-INSERTABLE CONNECTIONS

[75] Inventors: Kristin D. Johnson, Louisville, Colo.; Mark Alderton, Minneapolis, Minn.

[73] Assignee: Cardiac Pacemakers, Inc., St. Paul, Minn.

[21] Appl. No.: 09/056,283

[22] Filed: Apr. 7, 1998

[51] Int. Cl.[7] .............................. A61B 5/042; A61N 1/05
[52] U.S. Cl. .......................................... 600/375; 607/127
[58] Field of Search .............................. 600/375; 607/127

[56] References Cited

U.S. PATENT DOCUMENTS

| | | | |
|---|---|---|---|
| 4,026,303 | 5/1977 | Babotai | 607/127 |
| 4,827,940 | 5/1989 | Mayer et al. | 600/375 |
| 5,531,783 | 7/1996 | Giele et al. | 607/127 |

Primary Examiner—Lee Cohen
Attorney, Agent, or Firm—Schwegman, Lundberg, Woessner & Kluth, P.A.

[57] ABSTRACT

A helical element for insertion into tissue comprises a helical element having an insertion end, a protruding end and an open central area within the wire, rods, filaments, cables or the like that form the helix. The helical element has at least its insertion end covered by a cap of a water-soluble or water-dispersible composition. There is either a hollow area within the composition within the open central area or the material is more porous than the remaining material. The helical element preferably comprises an electrical lead, such as a positive endocardial lead, with an electrode at the protruding or distal end of the lead. The helical element may comprise any biocompatable material with sufficient structural integrity to provide a secure attachment to tissue in a patient. Where the helical element is also to provide an active (electrically active) function, the composition of the helical element should also be electrically conductive.

10 Claims, 1 Drawing Sheet

REMOVABLE CAP FOR TISSUE-INSERTABLE CONNECTIONS

BACKGROUND OF THE ART

1. Field of the Invention

The present invention relates to the field of insertable or implantable materials or devices in which the material or device is secured into the tissue of a patient through a helical or screw element which is secured into tissue or the like. In particular, the present invention relates to protective elements such as protective caps over a penetrating or pointed section of the material or device, wherein the protective element is capable of timely removal (as by dissolution) from the penetrating or pointed section during technical (e.g., medical) procedures.

2. Background of the Art

Many therapeutic or protective procedures for patients include the implantation of devices into a patient. Such implantations include drug delivery systems, electrostimulating devices (such as pacemakers or pain reduction devices), monitoring devices, electrical leads, electrodes, sensor elements, etc. These devices often have to be firmly secured within the patient to prevent movement of the device that would defeat or diminish its effectiveness. This is particularly true with electrical leads in pacing or defibrillation devices, which must be precisely located so that electrical stimulation is effective. There are a number of different formats for the securement of electrical leads in patients, including, but not limited to, clips, sutured attachment, corkscrew-like inserts (referred to as helical inserts), and other conventional securement formats found in mechanical systems.

A preferred means of securing leads is the helical insert such as found in the GUIDANT™ Sweet-Tip™ Model 4269 bipolar endocardial lead. This lead comprises a helical element having a base side (proximal end) with an electrode and a sharp tip on an insert side (a distal end) of the element. The pointed end penetrates tissue when a rotating motion is applied to the helical element, causing the element to puncture and or screw into the tissue, advancing the proximal end towards the tissue. The proximal end may have a relatively flat or convex electrical plate, electrode, sensing element (e.g., semiconductor, circuit board, pressure plate, etc.) or contact, and the advancing of the helical element into the tissue brings the contact into firm position with the tissue. In pacing or defibrillating devices, the electrical discharge passes through the electrode and/or into the helical connecting element. In some leads, the helical element is coated with an insulating polymer (which must also be biocompatible) to render the helical element inactive or passive (from the standpoint of discharge). Typical polymer coatings could include polyamides, polyurethanes, silicone resins, polyacrylates, hardened gelatin, and especially poly-para-xylylene (e.g., Parylene C).

These types of devices may be inserted into a patient by a number of different medical procedures. The less invasive or traumatic the procedure, the more desirable is that procedure. For example, although the electrodes may be inserted by open chest surgery, the delivery of the electrode through catheterization techniques through arteries or veins is much more preferred. The difficulties involved with passing a sharp element through the vasculature of a patient can be readily appreciated, especially where the path can be tortuous or partially clogged with deposits. To avoid damage to the patient, the GUIDANT™ Sweet-Tip™ Model 4269 bipolar endocardial lead provides a mannitol cap over the helical element in the lead. The mannitol cap provides a protective cover for the helical element which prevents the point of the helical element from scraping or puncturing interior walls of the vasculature or other tissue during introduction of the element to the patient. The mannitol effectively dissolves during the procedure, depending on the placement of the lead and other environmental factors, usually over the course of about 4 to 10 minutes. With certain lead designs and target locations, the leads can be inserted and used when there is only partial dissolution of the caps. This practice of providing caps on the leads has been effective in preventing damage to the patient during the introduction of the lead. Improper use of the lead, as by unauthorized immediate insertion, can lead to dislodgement or unsatisfactory pacing, which could occur with the misuse of any lead.

Other formats for delivering helical or barbed elements to secure an electrode into contact with appropriate tissue have utilized securing elements which are in a retracted position within the end of the delivered electrode. The retracted element is advanced into an exposed and operative position after positioning of the distal end of the electrode element within the patient. Advancement and exposure of the retracted element may be effected, for example, by winding or screwing a helical element through a hole in the most forward area of the electrode or by simply advancing a straight element through a hole.

There have been two areas identified by the present inventors where improvements may be made in the use of mannitol caps in the protection of helical leads or securing elements. Because of the physical shape of the helical element, mannitol present within the core of the helix tends to be dissolved out more slowly than desirable from within the helix and adjacent any electrode at the proximal end of the helical element. Additionally, any slowly dissolving mannitol that does remain within the confines or central area of the helix may have a tendency to slow down the advance of the helical element through the tissue until all of the mannitol in the core area has been removed. The lack of consistent rates of dissolution of the caps from the helical element, for example where the lead was prematurely positioned into soft tissue, tends to require surgeons to wait for a maximum length of time to provide assurance of the cap dissolution and proper electrical contact. Although neither of these considerations affect the in place performance of the connected leads, the reduction in procedural time by reducing or eliminating these effects is desired.

SUMMARY OF THE INVENTION

Helical connectors are provided with protective caps of an aqueous soluble or aqueous dispersible material wherein there is a hollow area or porous area of said material in a region within the enclosing region of the helix.

DETAILED DESCRIPTION OF THE INVENTION

Figure 1:
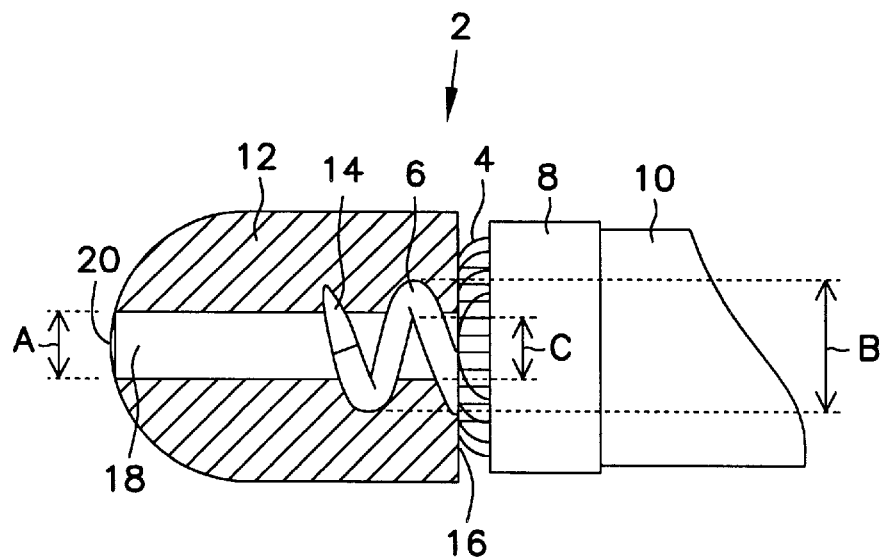
FIG. 1 shows an endocardial lead with a water soluble hollow cap.

The present invention describes a helical element, especially a helical element which can be securely inserted into electrical contact. The helical element for insertion into tissue may comprise a helical element, an electrical contact, and a support for the electrical contact. The helical element has an insertion end (e.g., an end which is to be inserted to secure the element) and a protruding end. The protruding end (the proximal end with respect to a supporting element) protrudes from or is attached to an electrical contact or is part of the electrical contact. There is an open central area within the wire, rods, filaments, cables or the like that form the helix of the helical element. The helical element having at least its insertion end covered by a cap of a water-soluble or water-dispersible composition. The open area within the helical element is either free of water-soluble or water-dispersible composition or contains a water-soluble or water-dispersible composition which dissolves more readily than the remainder of the composition which forms the cap. For example, the composition could be porous, fibrillated or the like, and composed of the same or different water-soluble or water-dispersible material. The helical element preferably comprises an electrical lead, such as a positive endocardial lead, with an electrode at the protruding or distal end of the lead.

The helical element may comprise any biocompatable material with sufficient structural integrity to provide a secure attachment to tissue in a patient. Where the helical element is also to provide an active (electrically active) function, the composition of the helical element should also be electrically conductive. With these features in mind, a wide range of materials may be selected by the user for the helical element, including, but not limited to, metals, metal oxides, ceramics, polymeric materials, composite materials, reinforced materials, and the like. Metals such as Nitinol, titanium, silver, gold, platinum, alloys, and the like are preferred.

As previously noted, the helical element may be coated with a protective or insulating layer to render the helical element inactive with respect to pacing discharges. Such coatings should be biocompatable such as polymer coatings including polyamides, polyurethanes, silicone resins, hardened gelatin, and especially poly-para-xylylene (e.g., Parylene C) and ceramic or composite coatings.

The composition of the cap material must meet the requirement that it is aqueous-soluble or aqueous-dispersible (blood being the aqueous system of choice for determining these physical properties). Preferably a 0.05 inch edge cube of the material in human blood at normal body temperature with light stirring should dissolve or disperse within ten minutes to meet this requirement. Natural sugars, saccharides, starches, other carbohydrates, polymers and the like are examples of materials which may be used for this cap material. It is particularly desirable that the cap material be non-toxic and preferably be biocompatible or even biodegradable or digestible. For example, mannitol, iditol, glucitol, rabitol, heptitol, octitol, arabinitol, betitol, bomesitiol, dambonitol, inositol, laminitol, ononitol, pinitol, sorbitol, non-crosslinked gelatin, poly(vinyl alcohol), poly (vinylpyrrolidone), soluble acrylates, soluble ethers, and soluble polyesters may be used in the practice of the present invention. Microfibers or biocompatible materials (e.g., microcellulose) held together by water-soluble water-dispersible binders may also be used in the practice of the present invention. Ingredients may also be present within these materials which increase the rate of dissolution, dispersion, or separation of the ingredients in the cap material, as is well known in the pharmaceutical tableting art.

It is also desirable in some circumstances to have the cap material carry active or therapeutic ingredients. For example, it is particularly desirable for the cap to carry anti-inflammatants, antibiotics, antiarrhythmic medication, and the like within the composition. These can thereby be locally delivered as the helical device is inserted into the patient and as the cap, e.g., mannitol, dissolves.

FIG. 1 shows an electrode element 2 according to the present invention. The electrode element 2 comprises an electrode 4 having a helical securement element 6. The electrode 4 is carried on a collar or support 8 which is in turn carried on a catheter or lead body 10 for delivery. An aqueous-soluble or dispersible cap 12 covers the helical element 6 and especially a pointed end 14 on the helical element 6. The cap 12 also abuts or lies flat against the contact surface 16 of the electrode 4. A hollow core 18 within the cap 12 is shown. The hollow core 18 has an outside diameter A which is less than the outside diameter B of the helical element 6. This assures that the cap 12 is retained against movement away from the electrode 4. There may optionally be, but not preferably, a cover layer 20 over the opening to the hollow core 18 to prevent tearing of the cap or collection of unwanted material within the core 18 during positioning of the electrode element 2. Although a closure of the cap may offer some advantages in avoiding collection of material within the open hole, it will act to slow the dissolution at least somewhat, and therefore is not preferred. The outside diameter A of the cap 12, the outside diameter (not specifically shown) of the electrode 4 and the collar 8 may be within the same general range of values, at about at least 0.001 inches, preferably from 0.002 to 0.25 inches or 0.005 to 0.20 inches, and more preferably from 0.005 to 0.100 inches. The helical element 6 may generally have an outside diameter B of about 0.001 to 0.07 inches, and an inside diameter C of from about 0.00075 to 0.008 inches. The outside diameter is of course larger than the inside diameter at all times. The central area of the helical element 6 which is defined by the inside diameter C is where the hollow core 18 or the porous material (not shown) within the central area extends. The cap 12 may generally have a length within a range of, for example, 0.05 to 0.25 inches, preferably from 0.09 to 0.15 inches, and more preferably from 0.095 to 0.135 inches. In place of the hollow core 18, a core of more readily dissolvable material (e.g., powdered, frothed or foamed mannitol or equivalent functioning soluble material), may be present. The helical element 6 will have an outside diameter of the dimensions previously noted. It is desirable that the mass of the cap 12 extends below the outside diameter of the helical element 6 rather than merely extending to that outer diameter so that there is some physical gripping by the material of the cap 12 within the helix itself. It is preferred that the mass of the cap extend between the outside diameter and inside diameter of the helical element 6, but it may extend beyond the inside diameter of the helical element 6 and still show improved dissolution rate benefits.

Figure 2:
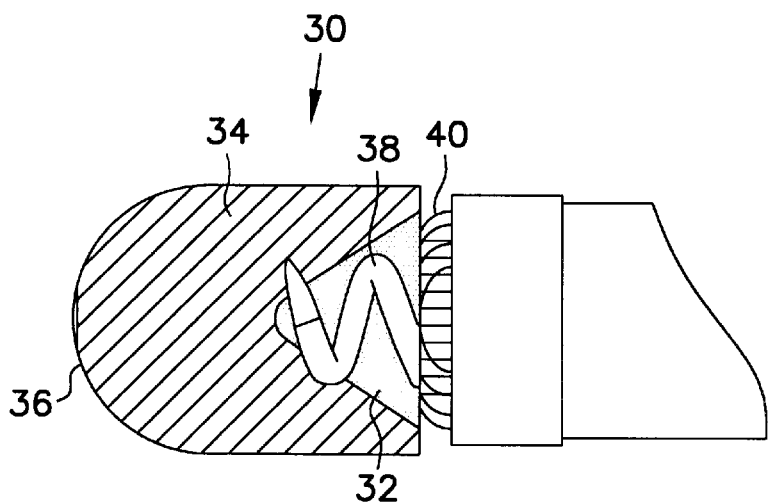
FIG. 2 shows an endocardial lead with a partially dissolved water soluble solid cap.

FIG. 2 shows an electrode element 30 of the prior art with a partially dissolved cap 32. The shaded area 34 represents material from the original cap 36 that has dissolved away, leaving the residue 32 within the helical element 38. It can be readily seen that the remaining core 32 would not only delay the ability of the helical element 38 to be inserted into tissue easily, but also that it would delay the time when the electrode 40 would be in flush electrical contact with tissue (not shown). As the cap would completely dissolve, the temporary presence of these materials merely delays the time when the electrode can be completely secured, but of course, does not affect its actual performance adversely or otherwise. When the cap is prematurely positioned within soft tissue, a mass of mannitol may remain on the tip of the helical element as the last to dissolve material, as opposed to being on the core. This is one reason why the use of a thin cover over the opening to the core is optional.

The article of the present invention may be manufactured as follows. A conventional electrode with a helical insertion tip may be used. A cap may be molded with the appropriate outside dimensions for the cap. The hollow section of the cap may then be formed, as by drilling, etching, or molding of the appropriate dimensions for the hole (being less than the outside diameter of the helical element). Additionally, a cap may be molded with a hole in the cap material (e.g., as by macaroni extrusion of a continuous tube), with cap sections cut off, and ends of the cap (where desired) closed off to form a closed cap. A Teflon or other release surface center core may be used to mold or extrude the cap material. Where the caps are first molded and a hole added, the hole may be added by selective dissolution of the material to form the hole, drilling or excavating of the hole, or pressing of a heated element into the cap material to remove material. Any method which is capable of producing the caps may be practiced in the present invention. After formation of the cap, the helical element is inserted into the cap, as by twisting or direct line pressure. The cap may be alternatively formed by the following procedures. The helical element is fitted with a removable rod within the core of the helix. A Teflon rod is desirable to assist in the ease of removal. The helical tip with the core therein is dipped or otherwise coated with the dissolvable material. After the cap has been formed by addition of the material onto the tip, the rod is removed. This leaves a hollow core within the helix as desired within the present invention. A more soluble material could be inserted into the helix either by first applying a limited amount of the more soluble material to fill the core of the helix, by pouring the more soluble material into an existing hole (as created by the removal of the rod), or by using a removable rod of more soluble material and not removing it.

Where a porous material is present within the core, rather than a hollow area, the core may either be first formed and the remainder of the cap built upon the porous core or a core excavated from the cap and the porous material added to the hollow area.

One beneficial aspect of the performance of the hollow-core caps of the present invention is the more direct control that the technician has over the timing of the use of the electrodes in the present invention. Not only does the cap dissolve off of the helical element more rapidly, but once there has been partial dissolution of the cap, the forces used to insert the helical element into the tissue cause the residual cap material to break off. When there was a core of material within the central area of the helix, that remaining material could not be broken off by the insertion forces. The technician would have to wait until the residual had been nearly completely dissolved away.

What is claimed:

1. A device for insertion into tissue comprising a helical element having an open central area and a water-soluble or water-dispersible cap for said helical element, the cap for said helical element having a hollow area which overlaps at least a part of said open central area and the cap extends within at least a portion of said central area, the cap extending below an outside diameter of the helical element so that the cap is gripped by the helical element, yet providing a hollow area within said helical element.

2. A device for insertion into tissue comprising:

1) a helical element having an open central area within the helical element and 2) a water-soluble or water-dispersible cap for said helical element, the cap for said helical element having a hollow area, the cap extending into at least a part of said open central area within the helical element and being gripped by the helical element.

3. The device of claim 2 wherein said helical element is attached to an electrode.

4. The device of claim 3 wherein said helical element is coated with an electrically insulating, biocompatible material.

5. The device of claim 2 wherein said cap comprises a water-soluble or water-dispersible carbohydrate.

6. The device of claim 2 wherein said cap comprises a water-soluble or water-dispersible material selected from the group consisting of mannitol, iditol, glucitol, rabitol, heptitol, octitol, arabinitol, betitol, bornesitiol, dambonitol, inositol, laminitol, ononitol, pinitol, sorbitol, non-crosslinked gelatin, and organic polymers.

7. The device of claim 2 wherein said cap comprises mannitol.

8. A device for insertion into tissue comprising a helical element having an open central area and a water-soluble or water-dispersible cap for said helical element, the cap for said helical element comprising a structure comprised of a water-soluble or water-dispersible composition used for the structure of the water-soluble or water-dispersible cap, said structure having a core area and at least a part of said core area comprising a second open central area filled with a composition which is more readily dissolved or dispersed than the composition used for the structure of the water-soluble or water-dispersible cap.

9. The device of claim 8 wherein said composition which is more readily dissolved or dispersed comprises a porous material.

10. The device of claim 9 wherein said porous material is the same composition as the water-soluble or water-dispersible composition used for the structure of the water-soluble or water-dispersible cap.

* * * * *